United States Patent [19]

Ezure et al.

[11] Patent Number: 5,364,794
[45] Date of Patent: Nov. 15, 1994

[54] PROCESS FOR PRODUCING SACCHARIDES

[75] Inventors: Yohji Ezure, Shiga; Shigeaki Maruo, Osaka; Katsunori Miyazaki, Iwate; Naoyoshi Yamada, Kyoto, all of Japan

[73] Assignee: Nippon Shinyaku Company Limited, Japan

[21] Appl. No.: 988,111

[22] PCT Filed: Jul. 24, 1991

[86] PCT No.: PCT/JP91/00984

§ 371 Date: Feb. 4, 1993

§ 102(e) Date: Feb. 4, 1993

[87] PCT Pub. No.: WO92/01805

PCT Pub. Date: Feb. 6, 1992

[30] Foreign Application Priority Data

Jul. 26, 1990 [JP] Japan .................. 2-198726
Feb. 5, 1991 [JP] Japan .................. 3-036776
Feb. 25, 1991 [JP] Japan .................. 3-053908

[51] Int. Cl.$^5$ ............... C12P 19/20; C12P 19/18; C12P 19/02; C12P 19/14
[52] U.S. Cl. ............... 435/96; 435/97; 435/98; 435/99; 435/101; 536/4.1; 536/17.4; 536/18.5; 536/18.6
[58] Field of Search .............. 435/101, 96, 97–99; 536/4.1, 17.4, 18.5–18.6

[56] References Cited

U.S. PATENT DOCUMENTS 3,878,191  4/1975  Fukumoto et al. .
5,256,788  10/1993  Ezure et al. .

FOREIGN PATENT DOCUMENTS 388003    9/1990   European Pat. Off. .
2125582   9/1972   France .
55-52078  11/1981  Japan .
58-63392  4/1983   Japan .
60-188065 9/1985   Japan .
61-30522  2/1986   Japan .
62-25977  2/1987   Japan .
62-87597  4/1987   Japan .
62-118885 5/1987   Japan .

Primary Examiner—Herbert J. Lilling
Attorney, Agent, or Firm—Rosenman & Colin

[57] ABSTRACT

A simplified process is provided for producing saccharides of definite chain length, such as glucose, maltose and maltooligosaccharides, each in an isolated state and with a high purity.

The process comprises transferring a saccharide chain, using a saccharide chain transferase, from a saccharide chain source to a substance substantially separable from the saccharides mentioned above and treating the thus-obtained oligosaccharide with an enzyme capable of excising the saccharide chain of definite chain length in an exo manner.

7 Claims, 7 Drawing Sheets

FIG. 1A  FIG. 1B  FIG. 1C
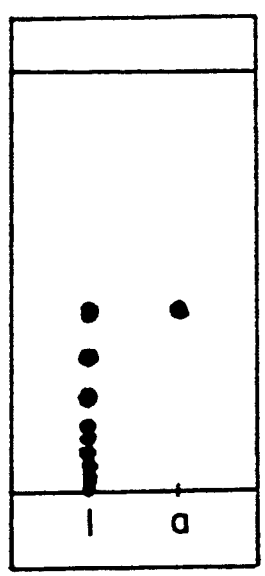
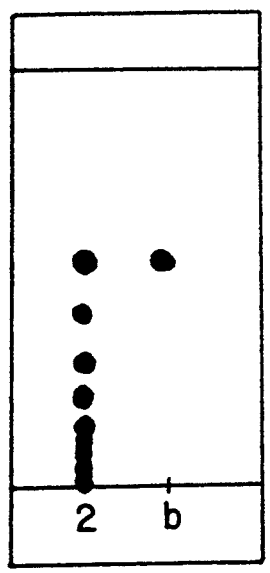
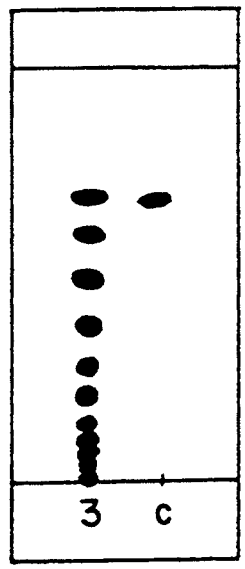
FIG. 1D  FIG. 1E  FIG. 1F
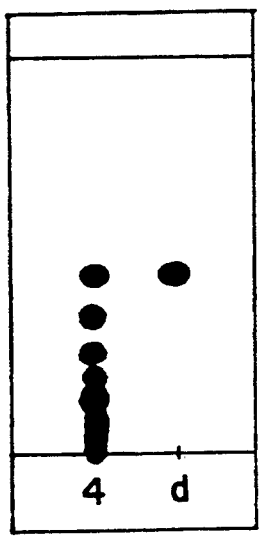
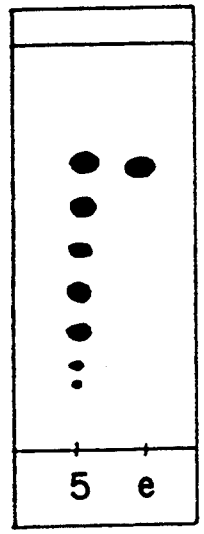
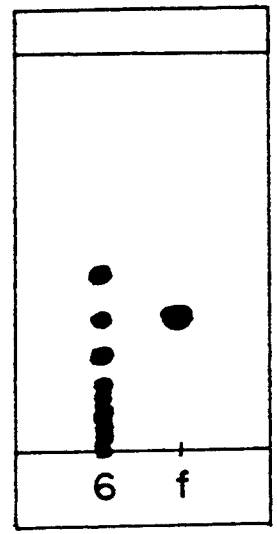

●: maltose-bound chitopearl
○: control

PROCESS FOR PRODUCING SACCHARIDES

TECHNICAL FIELD

This invention relates to a process for producing saccharides of definite chain length, such as glucose, maltose and maltooligosaccharides, each in an isolated and highly pure form.

BACKGROUND ART

Processes so far known for producing saccharides of definite chain length each in an isolated and highly pure form comprise hydrolyzing a glucan, such as starch, with one or more appropriate amylases and separating the desired saccharide from other unwanted oligosaccharides and/or monosaccharides by some or other known column chromatographic technique or the like [e.g. Denpun Kagaku Handbook (Starch Science Handbook), p. 452, 1987; Japanese Kokai Tokkyo Koho JP 57-209000; Japanese Kokai Tokkyo Koho JP 62-19210; Japanese Patent Publication No. 02-17158], and/or crystallizing the desired saccharide to thereby separate the same from other unwanted oligosaccharides and/or monosaccharides occurring in trace quantities (e.g. Denpun Kagaku Handbook, p. 456, 1987).

However, all the processes mentioned above intrinsically entail formation of such byproducts as glucose, uncleaved dextrin and other contaminant oligosaccharides and substantially fail to remove these unwanted saccharides from the reaction mixture.

It is known that the coexistence of an unwanted saccharide or saccharides in trace amounts markedly interfere with crystallization of the desired carbohydrate of definite chain length.

Furthermore, when the known processes mentioned above is employed for producing an oligosaccharide in a purity as high as possible, the production procedure becomes complicated, presenting problems from the yield and cost points of view.

DISCLOSURE OF INVENTION

Accordingly, the inventors of the present invention considered that these known production processes for saccharides have much to be improved and attempted to establish a process for producing a saccharide of definite chain length, such as glucose, maltose, or a maltooligosaccharide, in a form substantially free of unwanted saccharides, so that it may be suited for pharmaceutical use.

The gist of the invention lies in a serial and continuous execution of the following procedures.

Thus, the process of the invention comprises causing a saccharide chain to be transferred from a saccharide source, either directly or via an intermediate, to a substance substantially separable from the desired saccharide (hereinafter referred to as "separable substance") using a saccharide chain transferase, treating the resulting oligosaccharide with an enzyme capable of excising a saccharide chain of definite chain length therefrom in an exo manner (hereinafter referred to as "exo-cleaving enzyme") and isolating the desired saccharide of definite chain length.

In the following, the invention is described in detail.

The separable substance to be used in accordance with the invention is a carrier or support of the type currently in use as an immobilization carrier, such as chitosan beads, an ion exchange resin, a synthetic resin or the like, or a compound of the general formula [I]

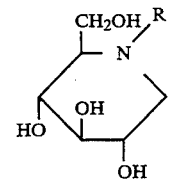

(wherein R is hydrogen, lower alkyl, hydroxyalkyl, phenylalkyl, phenylalkenyl, phenylalkynyl, phenoxyalkyl, phenoxyalkenyl or phenoxyalkynyl, including the case where the phenyl moiety is substituted) (hereinafter referred to as "a moranoline"), nojirimycin, an aminocyclitol, an aminocyclitol derivative, glucuronic acid, a glucosylated or oliogoglucosylated modification thereof or the like polar saccharide adsorbable on an ion exchange resin (hereinafter collectively referred to as "polar sugar"), or the like. The carrier may be in any form, e.g. bead-like, membrane-like or fibrous, for instance. Moranolines can be obtained from the mulberry white rind, actinomycetes and so on (e.g. Japanese Patent Application No. 54-159417, Japanese Patent Application No. 55-76838, Japanese Patent Publication No. 56-9919, Japanese Patent Application No. 57-93997, Japanese Patent Publication No. 59-27337). Glucosylated or oliogoglucosylated moranolines can be produced by the methods already disclosed [e.g. Agricultural and Biological Chemistry, 49, 2159 (1985)]. As for aminocyclitols, methods of obtaining them from validamycins have been disclosed (e.g. Japanese Patent Application No. 55-128157); they can also be prepared from commercially available validamycin preparations.

For a successful transfer of a saccharide chain to a carrier not having a terminal residue capable of being donated with such a cabohydrate chain by a saccharide chain transferase, such as glucosyl or a polar saccharide residue, it is necessary that an intermediate having a residue capable of receiving such a saccharide chain in the presence of a saccharide chain transferase be bound in advance to said carrier directly or via a spacer. As said intermediate, there may be mentioned polar sugars, monosaccharides such as glucose, oligosaccharides such as maltose and maltotriose, and so on. For binding such intermediate to a carrier, a method may be mentioned, for instance, which comprises binding maltose, a typical intermediate, to chitosan beads, a typical carrier, to which an amino-terminated spacer has been bound, using a reducing agent such as sodium cyanoborohydride (NaBH3CN). As examples of said spacer, there may be mentioned monofunctional and bifunctional substances generally used in the immobilization technology, such as oxirane, glutaraldehyde (GLA), etc.

As the saccharide chain transferase which can be used for the transfer of a saccharide chain from some other carbohydrate chain source, there may be mentioned, for example, cyclodextrin glycosyltransferase (CGTase), α-amylase, etc.

It has so far been reported that CGTase is produced by several bacterial strains such as, for example, Bacillus macerans, Bacillus megaterium, Bacillus circulans, alkalophilic Bacillus species and thermo-stable Bacillus species. While each of the cyclodextrins they produce has its characteristics, any type of CGTase may be used in the practice of the invention to satisfactorily achieve the purpose of the use thereof. It is known that, in addition to such enzymes, some microbial strains can directly produce carbohydrate chain transfer products (e.g. Abstracts of Papers read at the 1981 Annual Meeting of the Agricul-tural Chemical Society of Japan, 4N-2, published Mar. 10, 1981). Such microbial strains as such can also serve as saccharide chain transferases in the practice of the invention.

The pH and reaction temperature to be employed in the saccharide chain transfer reaction may vary to some extent depending on the specific saccharide chain transferase used. When CGTase, for instance, is used, the pH may range from 4.0 to 11.0 and is preferably 5.5 to 10.5, while the reaction temperature may range from 20°–85° C. and is preferably 45°–65° C. When CGTase is used as the saccharide chain transferase, the time required for the saccharide chain transfer reaction varies fairly much depending on the pH, reaction temperature, enzyme concentration and carbohydrate chain source concentration but, generally, is several hours to 4 days. As for the amount of CGTase to be used, it is to be understood that the larger the amount of the enzyme relative to a starch-related polysaccharide, which is the carbohydrate chain source, is, the better is the result obtainable. This is because it is desirable that as many saccharide chains as possible be transferred to the available residues by means of the saccharide chain transferase. More specifically, the enzyme is suitably used in an amount of 500–5,000 units (B.V. method), preferably 1,000–2,000 units, per gram of starch or starch-derived polysaccharide although said amount may vary depending on the saccharide chain source used (starch or a starch-derived polysaccharide), pH and reaction time.

As the saccharide chain source, there may be mentioned starch, starch-derived saccharides and cyclodextrins, among others. Any commercial grade of starch on the market may be used. Usable as the starch-derived saccharide are such intermediate hydrolyzates as various kinds of dextrin, amylose, and amylopectin, irrespective of degree of polymerization, high, medium or low. The concentration of starch or starch-derived saccharide is suitably 5–60%, preferably 10–20%, although it may vary depending on the treatment time and amount of transferase as selected to meet requests from the production side. For dextrin, 30 to 50% is practical. When starch is used as the carbohydrate chain source in a high concentration, however, the viscosity becomes so high that starch should be liquefied, prior to saccharide chain transfer reaction, by treatment with CGTase, α-amylase or the like. Further, for increasing the utilization of the starch or starch-derived polysaccharide added, the relative concentration thereof with respect to the transferase quantity should preferably be a little lower. For instance, the saccharide chain transferase is preferably used in an amount of 2,000–3,000 units per gram of starch or a starch-derived polysaccharide.

When a polar sugar is used as the separable substance, its concentration can be increased up to about 15% in the case of moranoline, for instance. However, it is effective to use the saccharide chain source in a weight ratio to moranoline of about 2–20.

When a carrier is used as the separable substance, the carrier bearing the saccharide chain after completion of the saccharide chain transfer reaction is generally washed thoroughly. It may also be a preferred procedure to deactivate the residual carbohydrate chain transferase after washing, for example by heating at 100° C. for 5 minutes and, further, thoroughly wash the saccharide chain-bearing carrier. The saccharide chain transferase used can be readily recovered by ultrafiltration (hereinafter referred to as "UF"), for instance.

When a polar sugar is used as the separable substance, the polar sugar, with and without a glucose oligomer, is adsorbed on an ion exchange resin after completion of the saccharide chain transfer reaction. In this case, too, the saccharide chain transferase used can be readily recovered by the UF method, for instance. When the recovery of the saccharide chain transferase is omitted, the reaction mixture as such is treated with an appropriate ion exchange resin. When said recovery is conducted, the reaction mixture is subjected to UF membrane treatment and the filtrate is treated with an ion exchange resin. As said ion exchange resin, there may be mentioned Dowex 50W-X2 (registered trademark), Diaion SA-11A (registered trademark) and Amberlite IR-120 (registered trademark), among others. The ion exchange resin to be used is suitably selected from among them according to the polarity of the polar sugar. It goes without saying that the amount of the ion exchange resin should be increased or decreased depending on the amount of the polar sugar submitted to the reaction. After adsorption of the polar sugar and the sugar carrying a glucose oligomer transferred thereto, the resin is generally subjected to thorough washing. And, after washing, the sugars are generally eluted from the ion exchange resin with 1N aqueous ammonia, for instance.

Then, treatment with an exo-cleaving enzyme is carried out at a pH suited for the exo-cleaving enzyme, generally at a reaction temperature of 30°–55° C. for several hours to 2 days. As the exo-cleaving enzyme, there may be mentioned glucoamylase, β-amylase and maltooligosaccharide-producing enzymes, among others. For producing maltose, for instance, β-amylase can be used. In that case, it is appropriate to adjust the reaction mixture to a pH of 4.5–6.0, for example 4.8, which is suited to β-amylase, then add β-amylase to the reaction mixture and conduct the reaction at a temperature of 30°–60° C. for 1-2 days. The amount of the exo-cleaving enzyme may depend on the kind and level of addition of the exo-cleaving enzyme used and/or the separable sub-stance. When the separable substance is a carrier, addition of 20–100 units of the enzyme per milliliter of the carrier makes it possible to finish the cleavage step within the daily working hours.

When a polar sugar is used as the separable substance and elution from the ion exchange resin is performed following the procedure mentioned previously, the desired saccharide of definite chain length can be isolated substantially selectively by subjecting the reaction mixture following exo-cleaving enzyme treatment, either as such or after separation of the exo-cleaving enzyme by an appropriate separation method, for example the UF membrane method, again to treatment on an ion exchange resin capable of adsorbing the polar sugar used. It is necessary to adjust the amount of the resin according to, in the main, the quantity of the polar sugar feed.

When a polar sugar is used as the separable substance and the exo-cleaving enzyme treatment is carried out without prior elution from the ion exchange resin by the procedure mentioned above, or when a carrier is used as the separable substance, the desired saccharide of definite chain length can be isolated substantially selectively by separating the exo-cleaving enzyme from the reaction mixture following exocleaving enzyme treatment by an appropriate separation method, for example filtration or the UF membrane method.

The exo-cleaving enzyme separated in the above manner can be reused.

The liquid phase finally obtained can be concentrated by any of concentration means in general use, for example by the reduced pressure concentration method using a rotary evaporator, or the reverse osmosis (RO) membrane method.

When a polar sugar is used as the separable substance, the sugar chain transferase and exo-cleaving enzyme each can be used either in the form of a solution or in the form of an immobilized enzyme prepared by a per se known method generally used for producing immobilized enzymes. Particularly when a crude enzyme is used, the use of an immobilized enzyme can reduce the amount of contaminants and therefore offers an advantage in the purification step.

The reactions involved in the production of maltose by the process of the present invention may be schematically shown in the following.

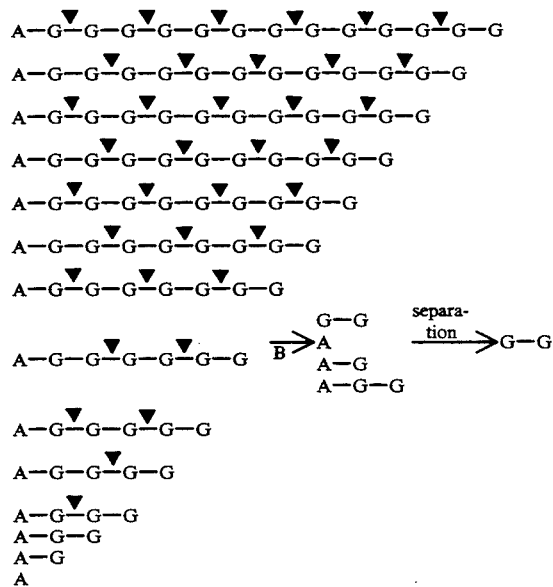

(in the above illustration, A represents a separable substance, G glucose, and B β-amylase. All A's are not always the same. The mark ▼ indicates the site of cleavage by β-amylase.)

As illustrated above, β-amylase, by its nature, leaves disaccharides or trisaccharides uncleaved (in the case illustrated above, G-G, A-G and A-G-G). Therefore, the neutral saccharide in solution, namely maltose (G-G), alone can be readily isolated from the other constituents of the reaction mixture (A, A-G and A-G-G), which are solid or polar, by filtration or ion exchange resin treatment, for instance.

After separation of maltose, the saccharide chain transferase can cause saccharide chain extension again on the other residues. Thus, as the above saccharide chain transfer, cleavage reaction and separation are repeated, eventually a continuous production of maltose is consumated.

In view of the foregoing, the production process of this invention can be said to be a novel and epochal production process by which a desired saccharide of definite chain length alone can be obtained substantially selectively in an isolated state and, at the same time, in a continuous manner. In accordance with the invention, it is also possible to enjoy the advantage that a desired saccharide of definite chain length alone can be obtained but also further advantages such that the production steps are very simple as compared with the prior art processes, that the cost and labor, among others, can be much reduced, and that the yield can be increased to a satisfactory extent.

Among the saccharides obtainable by the process of the invention, maltose, for instance, is useful in the pharmaceutical field where a particularly high purity is required. Thus, it is used in the form of drip infusion fluids, for instance. Naturally, it can be used in the food industry. Maltotriose, maltotetraose, maltopentaose, maltohexaose and the like can be used as diagnostic reagents and the like. Furthermore, since the use of purer maltose as the raw material in producing maltitol, a sweetener, by reduction thereof results in better crystallization of maltitol, the maltose produced by the process of the invention is very advantageous in that respect as well.

As examples of application, in the pharmaceutical field, of the saccharides obtainable by the process of the invention, there may be mentioned infusion fluids, among others. When employed in infusion fluids, maltose gives an isotonic solution at a concentration of 10%, which has a caloric value twice higher as compared with glucose on an equal volume basis and, for these and other reasons, maltose is known to be more beneficial than glucose or the like ("Masui to Sosei", vol. 20, No. 3, page 163, 1984). Similarly, a 15% maltotriose solution, which is isotonic, is three times higher in caloric value as compared with glucose, hence is still more efficient. In applying the saccharides produced by the process of the invention to the pharmaceutical field, the composition given below, for instance, may be employed. Generally, infusion fluids can contain the saccharide (e.g. maltotriose, maltotetraose, maltopentaose, maltohexaose) alone or together with glucose or maltose, optionally in combination with an inorganic salt or salts such as sodium chloride, potassium chloride, sodium acetate, etc. (Example of infusion fluid composition)

Maltotriose 15 g, potassium chloride 0.03 g, calcium chloride 0.02 g, sodium chloride 0.6 g and sodium lacerate 0.31 g are mixed and this composition is used to prepare 100 ml of an infusion fluid.

BEST MODES FOR CARRYING OUT THE INVENTION

The following reference examples and working examples illustrate the present invention in further detail and more specifically but these are by no means limitative of the scope of the invention.

BRIEF DESCRIPTION OF THE DRAWINGS

FIGS. 1A–1F shows the TLCs of the saccharide chain transfer products obtained in Example 1. In the figures, the FIG. 1A, 1 indicates the saccharide chain transfer based on moranoline, FIG. 1B, 2 that based on N-methylmoranoline, FIG. 1C, 3 that based on N-benzylmoranoline, FIG. 1D, 4 that based on N-hydroxyethylmoranoline, FIG. 1E, 5 that based on N-butylmoranoline and FIG. 1F, 6 that based on glucosylmoranoline, while a, b, c, d, e and f represent the corresponding moranolines as standards.

FIG. 8-B shows the results obtained in Example 7. ● indicates the case where the maltose-bound Chitopearl was used and o the case where untreated Chitopearl was used. The ordinate indicates the absorbance of the solution and the abscissa the time (in hours).

Reference Example 1

Preparation of Immobilized CGTase Beads

Figure 2:
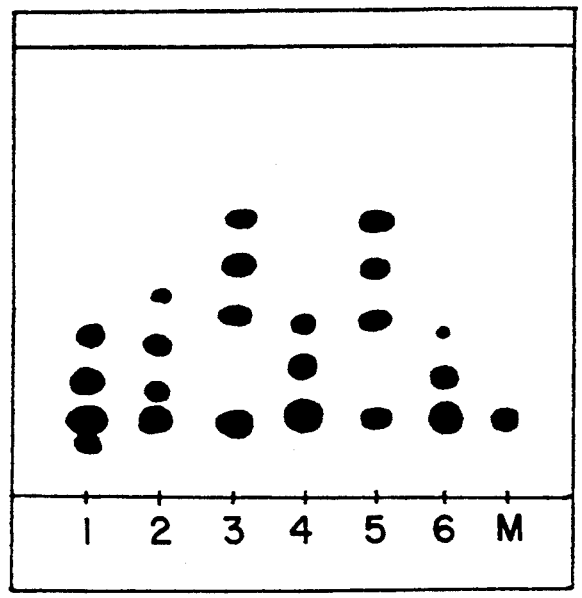
FIG. 2 shows the TLCs of the β-amylase treatment mixtures obtained in Example 1. In the figure, 1, 2, 3, 4, 5 and 6 are as explained with respect to FIG. 1. M indicates maltose.

First, 200 ml of Bacillus macerans-derived CGTase (Contizyme, product of Amano Pharmaceutical Co.) was dialyzed against 0.01M acetate buffer (pH 6.0). Separately, 50 ml of Chitopearl BCW-3010 (registered trademark, product of Fuji Spinning Co.; hereinafter the same shall apply) was gently shaken in 0.1M acetate buffer (pH 5.0) containing 2.5% glutaraldehyde at room temperature for 24 hours and then thoroughly washed with water. To this activated Chitopearl was added the supernatant obtained by centrifugation of the above-mentioned dialyzate, the mixture was gently shaken at 4° C. for 16 hours for causing binding of the enzyme, and the Chitopearl was thoroughly washed with water. This procedure gave the intended immobilized enzyme containing 23.8 mg of protein/ml of beads.

Reference Example 2

Preparation of Immobilized β-amylase.

First, 4.8 ml of sweet potato-derived β-amylase (product of Sigma, suspension in ammonium sulfate solution) was dialyzed against 0.01M acetate buffer (pH 5.0). Separately, 10 ml of Chitopearl BCW-3010 was gently shaken in 0.1M acetate buffer (pH 5.0) containing 2.5% glutaraldehyde at room temperature for 24 hours and then thoroughly washed with water. To this activated Chitopearl was added the supernatant obtained by centrifugation of the above dialyzate, the mixture was gently shaken at 4° C. for 16 hours for effecting binding of the enzyme, and the Chitopearl was then thoroughly washed with water. Thus was obtained the intended immobilized enzyme containing 6.44 mg of protein/ml of beads.

Reference Example 3

Preparation of a Carrier by Binding Maltose to Chitosan Beads

Chitopearl BCW-3010 (5 ml), as chitosan beads, and 1.8 g of maltose were added to 20 ml of a mixed solvent composed of methanol/water=1/1 and, after dissolution of maltose, sodium cyanoborohydride was added. The pH was adjusted to 3 to 4 and the reaction was carried out for 3 days. The beads were collected by filtration and thoroughly washed with water to give the intended carrier.

Reference Example 4

Preparation of Immobilized Glucoamylase

Glucoamylase ("Gluczyme NL-3", product of Amano Pharmaceutical; 35 liters) was diluted by addition of 35 liters of deionized water and purified by the UF method, and the thus-obtained enzyme concentrate was introduced into a column packed with 33 liters of Chitopearl BCW-3010 for enzyme adsorption. Thus, the enzyme concentrate was adjusted so that it finally became 56 liters of a solution in 0.05M acetate buffer (pH 5.0). This solution was circulated through the column at 8° C. for 24 hours for effecting enzyme adsorption, the column was then washed with 150 liters of 0.05M acetate buffer (pH 5.0), and 120 liters of 0.05M acetate buffer (pH 5.0) containing 2.5% glutaraldehyde was circulated through the column for completion of immobilization. The excess glutaraldehyde was removed by passing 550 liters of water through the column. Thus was obtained the intended immobilized enzyme containing 24.4 mg of protein/ml of beads.

EXAMPLE 1

In 50-ml Erlenmeyer flasks were respectively placed 300 mg each of moranoline, N-methylmoranoline, N-benzylmoranoline, N-hydroxyethylmoranoline, N-butylmoranoline and glucosylmoranoline. To each of these flasks was added 1,200 mg of soluble starch and the mixture was dissolved by addition of 10 ml of water with warming. Then, 5 ml of the immobilized CGTase-carrying beads prepared by the procedure of Reference Example 1 was added and the transfer reaction was conducted at 40° C. for 3 days with shaking. Then, 3 ml of each reaction mixture was sampled and applied to 10 ml of the strong acidic ion exchange resin Dowex 50W-X2 and after the resin was thoroughly washed with water, elution was carried out with 60 ml of 1N ammonium hydroxide. The eluate was concentrated to dryness using a rotary evaporator. The weights of the respective saccharide chain transfer products are shown in Table 1. TLCs of the respective products (Kieselgel 60F254,Merck; developing solvent: n-propanol/ammonium hydroxide/water=6/2/1; color developer: spraying with 10% ethanolic sulfuric acid, followed by heating over a flame; hereinafter the same shall apply) are shown in FIGS. 1A–1F.

Then, each saccharide chain transfer product was dissolved in water to a concentration of 50 mg/ml and the solution was adjusted to pH 5–6 with 2N hydrochloric acid. The immobilized β-amylase prepared by the procedure of Reference Example 2 (200 beads) was then added and the reaction was conducted at 37° C. for 5 hours. TLCs of the thus-obtained β-amylase digestion mixtures are shown in FIG. 2.

From FIG. 2, the formation of maltose in the respective reaction mixtures is evident.

Each β-amylase digestion mixture was then applied to 10 ml of the strongly acidic ion exchange resin Dowex 50W-2X, and the effluent was neutralized with 2N sodium hydroxide and then concentrated to dryness using a rotary evaporator. The weights of maltose thus obtained are shown in Table 1.

TABLE 1

| No. | Polar sugar | Carbohydrate chain transfer product (mg) | Weight of maltose (mg) |
|---|---|---|---|
| 1 | Moranoline | 159 | 66 |
| 2 | N-Methylmoranoline | 122 | 29 |
| 3 | N-Benzylmoranoline | 98 | 23 |
| 4 | N-Hydroxemoranoline | 160 | 57 |
| 5 | N-Butylmoranoline | 100 | 24 |
| 6 | N-Glycosylmoranoline | 110 | 52 |

Figure 3:
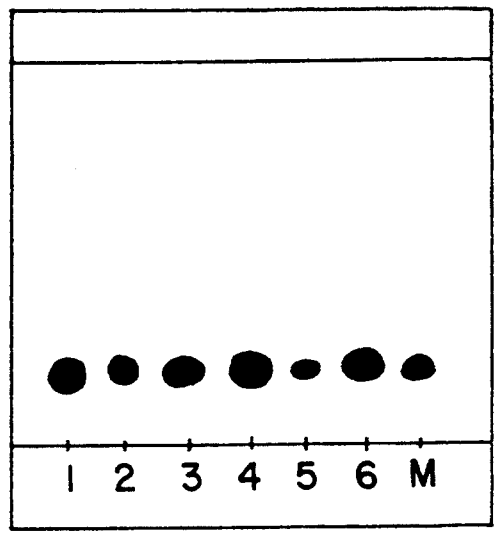
FIG. 3 shows the TLCs of the maltose fractions obtained in Example 1. In the figure, 1, 2, 3, 4, 5 and 6 are as explained with respect to FIG. 1. M indicates maltose.

TLCs of these maltose fractions are shown in FIG. 3.
From FIG. 3, it is evident that maltose alone was produced.

EXAMPLE 2

Figure 4:
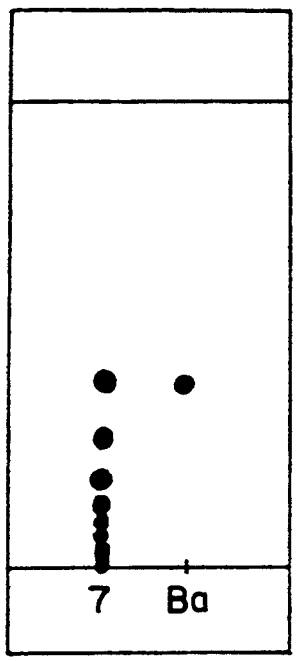
FIG. 4. shows the TLC of the saccharide chain transfer product obtained in Example 2. 7 indicates the validamine-based saccharide chain transfer product while Ba represents validamine.

A 50-ml Erlenmeyer flask was charged with 60 mg of validamine and 1,200 mg of soluble starch, and after addition of 10 ml of water, the mixture was warmed for effecting dissolution. To the solution were added 5 ml of the immobilized CGTase beads prepared by the procedure of Reference Example 1, and the transfer reaction was carried out at 40° C. for 3 days with shaking. Then, 3 ml of the reaction mixture was taken and applied to 10 ml of the strongly acidic ion exchange resin Dowex 50W-X2, and after the resin was thoroughly washed with water, elution was carried out with 60 ml of 1N ammonium hydroxide, and the eluate was concentrated to dryness using a rotary evaporator. The weight of this saccharide chain transfer product was 274 mg. A TLC of the saccharide chain transfer product is shown in FIG. 4.

To this saccharide chain transfer product was added 5.5 ml of water and after the pH was adjusted to 5–6 with 2N hydrochloric acid, the immobilized β-amylase (200 beads) prepared by the procedure of Reference Example 2 was added and the reaction was conducted at 37° C. for 5 hours. A TLC of this β-amylase digestion mixture is shown in FIG. 5.

Figure 5:
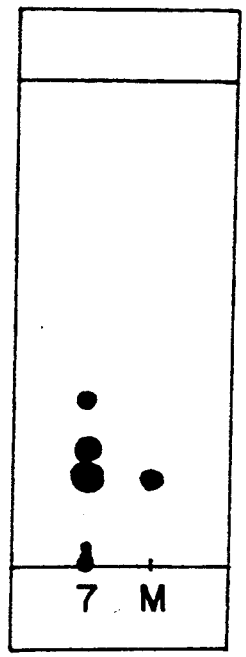
FIG. 5 shows the TLC of the β-amylase reaction mixture obtained in Example 2. 7 indicates the validamine-based saccharide chain transfer product and M indicates maltose.

From FIG. 5, maltose formation is evident.

This β-amylase digestion mixture was then applied to 10 ml of the strongly acidic ion exchange resin Dowex 50W-X2, and the effluent was neutralized with 2N sodium hydroxide and concentrated to dryness using a rotary evaporator. The weight of maltose obtained was 113 mg. A TLC of this maltose fraction is shown in FIG. 6.

Figure 6:
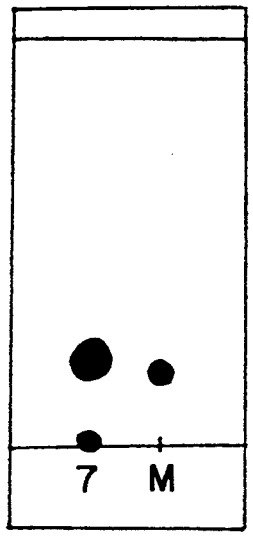
FIG. 6 shows the TLC of the maltose fraction obtained in Example 2. 7 indicates the validamine-based saccharide chain transfer product and M indicates maltose.

From FIG. 6, it is evident that maltose alone was produced. Example 3.

To a test tube equipped with a screw cap were added 60 mg of N-(1,3-dihydroxy-2-propyl)valiolamine, 240 mg of the enzymatically prepared dextrin "Amycol" (registered trademark, product of Nihon Denpun) and, further, 1 ml of CGTase "Contizyme" (product of Amano Pharmaceutical), followed by addition of water to make a total of 2 ml. The transfer reaction was carried out at 50° C. for 48 hours with shaking. The whole reaction mixture was passed through about 10 ml of the strongly acidic ion Exchange resin Dowex 50W-X2 and after the resin was thoroughly washed with water, elution was carried out with 60 ml of 1N ammonium hydroxide. The eluate was concentrated to dryness using a rotary evaporator. The thus-obtained saccharide chain transfer product weighed 118.6 mg.

To this saccharide chain transfer product was added 10 ml of 0.1M acetate buffer (pH 4.8) for dissolution, and 100 μl of β-amylase (derived from sweet potato, suspended in ammonium sulfate solution; product of Seikagaku Corp.) was then added. The reaction was conducted at 37° C. for 16 for hours and the resulting β-amylase digestion mixture was applied to 10 ml of the strongly acidic ion exchange resin Dowex 50W-X2. The effluent and washings were combined, neutralized with 2N sodium hydroxide and concentrated to dryness using a rotary evaporator to give 129.8 mg of maltose.

EXAMPLE 4

Oligoglucosylmoranoline (4.7 g) was dissolved in 170 ml of water, and after the solution was adjusted to pH 4.9 with 1N hydrochloric acid, 1 ml of β-amylase (product of SERVA, derived from sweet potato; 848 U/mg protein, recrystallized three times, 5 mg/ml) was added, and the reaction was carried out at 37° C. for 20 hours. The reaction mixture was passed through 30 ml of the strong basic ion exchange resin Diaion SA-11A and the resin was then thoroughly washed with deionized water. The effluent and washings were combined and passed through 50 ml of the strongly acidic ion exchange resin Dowex 50W-X2. The resin was thoroughly washed with deionized water. The effluent and washings were combined and concentrated to dryness to give 1.4 g of a powder.

The maltose content of this powder as determined by high-performance liquid chromatography (column: Nucleosil 5NH$_2$, 5 μm, 4 mm i.d.×25; mobile phase: acetonitrile/water=70/30; detection: differential refractometer) was 98.3%.

EXAMPLE 5

Soluble starch (15 g) was dissolved in 100 ml of water with warming and then 5 g of moranoline was dissolved in the solution. After the whole volume was made up to 170 ml with water, 20 ml of the immobilized CGTase beads prepared by the procedure of Reference Example 1 was added and the reaction was carried out at 55° C. for 42 hours. Then, the immobilized CGTase beads were filtered off and washed with water. The filtrate and washings were combined and passed through 50 ml of the strong acidic ion exchange resin Dowex 50W-X2. After the resin was thoroughly washed with water, elution was carried out with 1N ammonium hydroxide, and the eluate was lyophilized to give 11.3 g of a powder.

This powder was dissolved in 250 ml of water and after the solution was adjusted to pH 5.0 with 2N hydrochloric acid, 10 ml of the immobilized β-amylase prepared by the procedure of Reference Example 2 was added, and the reaction was conducted at 37° C. for 3 hours. The immobilized β-amylase was filtered off and washed with water. The filtrate and washings were combined and passed through 30 ml of the strong basic ion exchange resin Diaion SA-11A, and the resin was thoroughly washed with water. Then, the effluent and washings were combined and concentrated to about 20 ml under reduced pressure and passed through 100 ml of the strong acidic ion exchange resin Dowex 50W-X2. After washing the resin slightly, the effluent and washings were combined and lyophilized to give 800 mg of a maltose powder.

Figure 7:
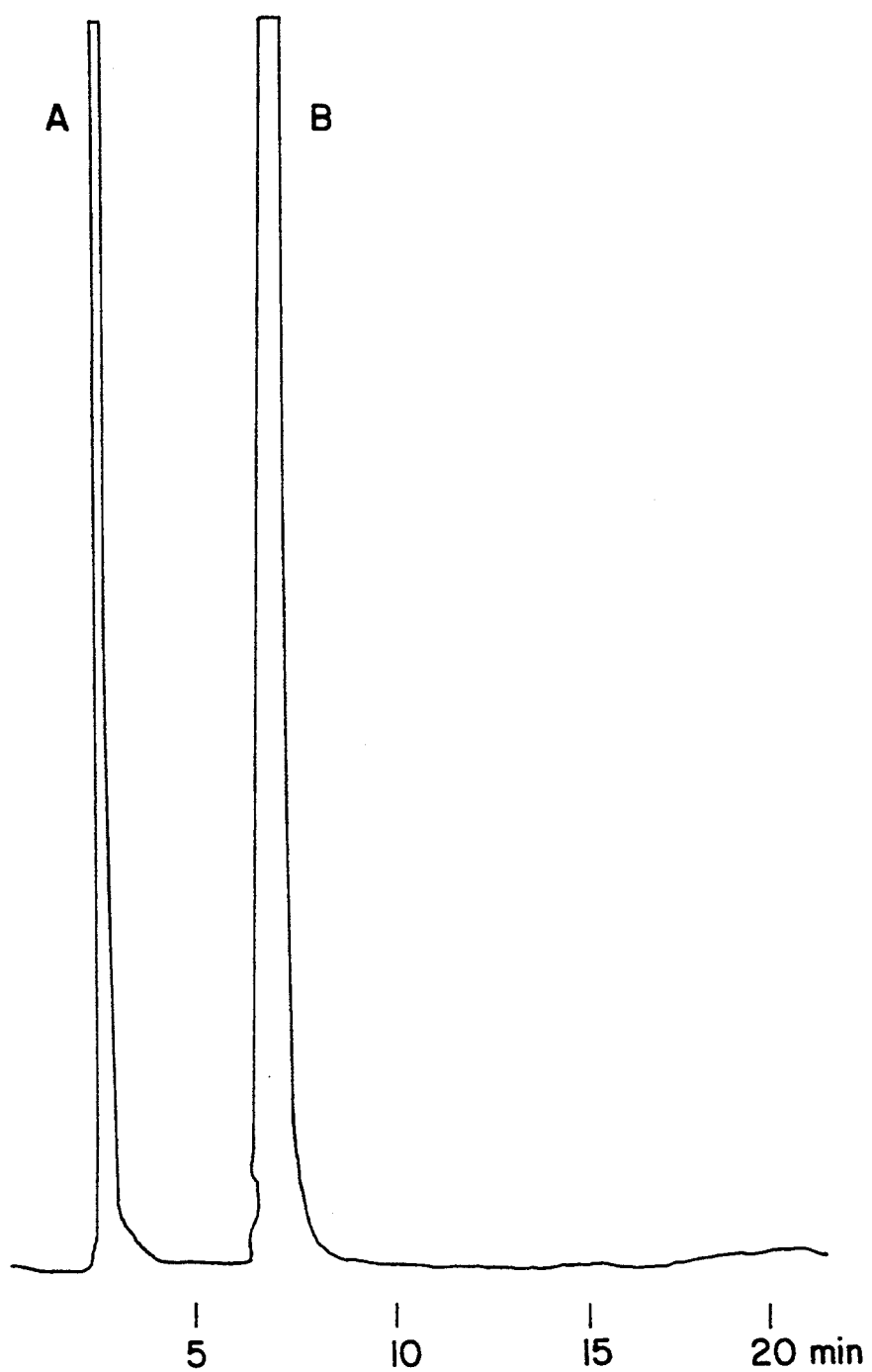
FIG. 7 shows the high-performance liquid chromatogram of the maltose powder obtained in Example 5. In the figure, A indicates the solvent peak and B the maltose peak.

Analysis of this product by high-performance liquid chromatography under the same conditions as used in Example 4 using 10 μl of a solution having a maltose concentration of 85 mg/ml revealed that said product was 100%-pure maltose, as shown in FIG. 7.

EXAMPLE 6

To 5 ml of the maltose-bound Chitopearl prepared in Reference Example 3 were added 3 g of the enzymatically prepared dextrin "Amycol" (registered trademark, product of Nichiden Kagaku) and 10 ml of water. After adjusting the pH to 6.0 with 2N hydrochloric acid, 5 ml of CGTase (Contizyme, product of Amano Pharmaceutical) was added, and the whole mixture was gently shaken at 50° C. for 24 hours. Then, the carrier beads were filtered off, thoroughly washed with water, heated in boiling water at 100° C. for 5 minutes and, again, thoroughly washed with water.

Separately, as a control, the above procedure was followed using untreated Chitopearl in lieu of the maltose-bound Chitopearl.

To 5 ml of the thus-obtained carrier beads was added 10 ml of 0.2M acetate buffer and, after addition of 50 μl of β-amylase (product of SERVA), the resultant mixture was gently shaken at 37° C.

Figure 8A:
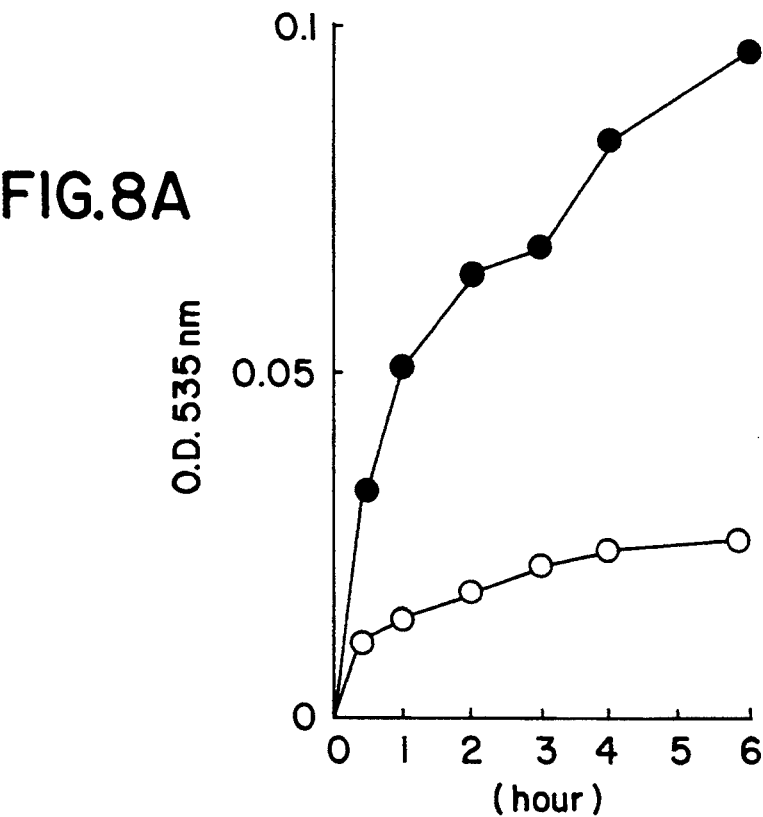
FIG. 8-A shows the results obtained in Example 6. ● indicates the case where the maltose-bound Chitopearl was used and o the case where untreated Chitopearl was used. The ordinate indicates the absorbance of the solution and the abscissa the time (in hours).
Figure 8B:
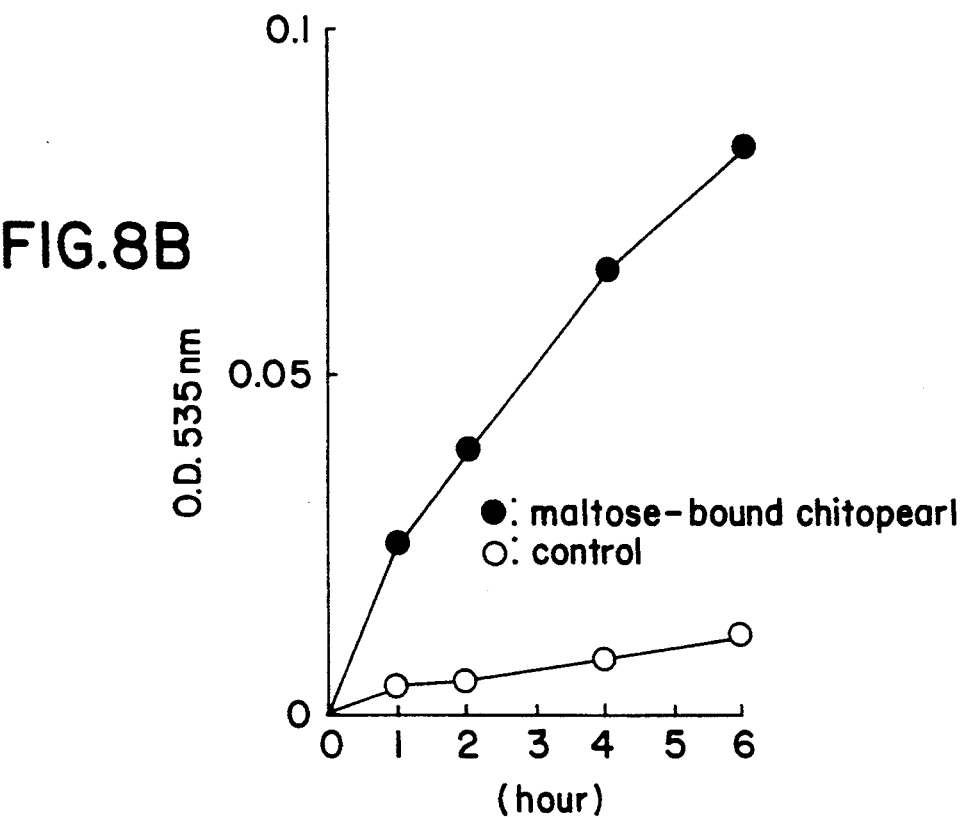
Figure 9:
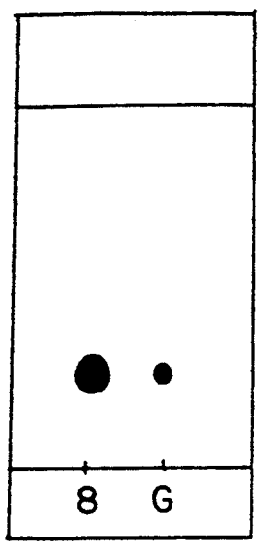
FIG. 9 shows the TLC of the glucose fraction obtained in Example 8. In the figure, 8 indicates the glucose fraction and G glucose.

The reaction mixture was sampled at timed intervals (sample size 500 μl). To each sample was added 1 ml of 3,5'-dinitrosalicylic acid test solution. The mixture was heated in boiling water at 100° C. for 10 minutes and then ice-cooled and, after addition of 5 ml of water, the absorbance at 535 nm was measured for assaying maltose liberated. The results thus obtained are shown in FIG. 8-A.

In the case of the maltose-bound Chitopearl, maltose liberation was more evident as compared with untreated Chitopearl. The supernatant separated after this β-amylase treatment was concentrated and analyzed by TLC. Maltose alone was detected; the occurrence of other oligosaccharides was not noticed.

EXAMPLE 7

The maltose-bound Chitopearl used in Example 6 and remaining after β-amylase cleavage and the control Chitopearl were respectively heat-treated at 100° C. for 5 minutes and thoroughly washed with water. Each of them (50 ml each) was and added to a 50-ml Erlenmeyer flask, together with 3 g of the enzymatically prepared dextrin "Amycol" (registered trademark, product of Nihon Denpun), 10 ml of water and 5 ml of CGTase "Contizyme" (product of Amano Pharma-ceutical), and the reaction was carried out again with shaking at 50° C. for 24 hours. The beads were then recovered by filtration, washed, heat-treated at 100° C. for 5 minutes and, further, thoroughly washed with water.

These beads (5 ml) were added to 10 ml of 0.2M acetate buffer (pH 4.8) and, after further addition of 50 μl of β-amylase (derived from sweet potato, suspended in ammonium sulfate solution, product of Seikagaku Corp.), the mixture was incubated at 37° C. The reaction mixture was sampled at timed intervals (sample size 0.5 ml). To each sample was added 1 ml of 3,5-dinitrosalicylic acid test solution. The mixture was heated in boiling water at 100° C. for 5 minutes and then ice-cooled and, after addition of 5 ml of water, the absorbance at 535 nm was measured for assaying the maltose liberated. The changes in absorbance thus found are shown in FIG. 8-B.

As is evident from FIG. 8-B, satisfactory maltose formation was noticed, as in the first reaction in Example 1, as compared with the control.

It was thus suggested that maltose production could be repeated using the maltose-bound beads; namely the possibility of continuous production was suggested.

EXAMPLE 8

The same moranoline-based saccharide chain transfer product (149 mg) as that obtained in Example 1 was dissolved in 3 ml of water, and after the solution was adjusted to pH 5.0 with 2N hydrochloric acid, the immobilized glucoamylase beads (200 beads) prepared in Reference Example 4 were added, and glucose liberation was effected by shaking at 40° C. for 4 hours. This reaction mixture was applied to 10 ml of Dowex 50W-X2, and the effluent (unadsorbed fraction) was neutralized with 2.5N sodium hydroxide and then concentrated to dryness to give 58.3 mg of pure glucose.

Its TLC is shown in FIG. 7.

EXAMPLE 9

Figure 10:
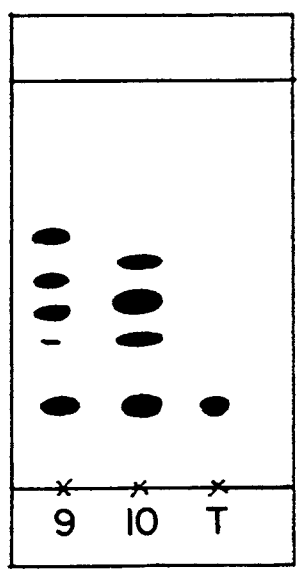
FIG. 10 shows the TLCs of the maltotriose-producing amylase reaction mixtures obtained in Example 9. In the figure, 9 indicates the N-propylmoranoline-based and 10 the N-benzylmoranoline-based saccharide chain transfer product, and T indicates maltotriose.

An N-propylmoranoline-based or N-benzylmoranoline-based saccharide chain transfer product (12.5 mg) obtained in the same manner as in Example 1 was dissolved in 250 μl of water and the solution was adjusted to pH 6.0 with 2N hydrochloric acid. Then, 250 μl of a solution of a maltotriose-producing amylase (95 units/0.25 mg protein; one unit is the quantity of enzyme forming 1 mg of a reducing sugar corresponding to maltotriose per hour) was added and maltotriose formation was effected with gentle shaking at 40° C. for 2 hours. A TLC of this reaction mixture is shown in FIG. 10.

Further, this reaction mixture was applied to Dowex 50W-X2 and the effluent (unadsorbed fraction) was neutralized with 2.5N sodium hydroxide. A TLC of this maltotriose fraction is shown in FIG. 11.

Figure 11:
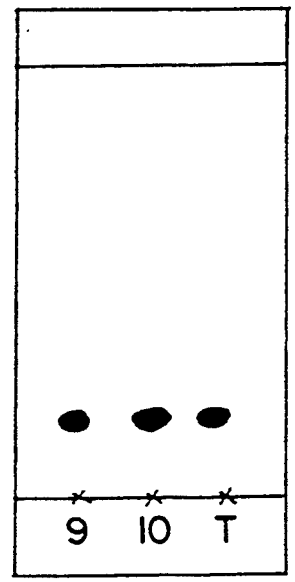
FIG. 11 shows the TLCs of the maltotriose fractions obtained in Example 9. In the figure, 9 indicates the maltotriose fraction from the N-propylmoranoline-based chain transfer product, 10 the maltotriose fraction from the N-benzylmoranoline-based product, and T maltotriose.

From FIG. 11, it is evident that maltotriose alone was produced.

Analysis by the 3,5-dinitrosalicylic acid method using a reference standard of maltotriose revealed the formation of 5.2 mg and 5.7 mg, respectively, of maltotriose.

EXAMPLE 10

An N-propylmoranoline-based or N-benzylmoranoline-based saccharide chain transfer product (to 12.5 mg) obtained in the same manner as in Example 1 was admixed with 250 μl of a solution of a maltotetraose-producing amylase (26.25 units/0.24 mg protein; one unit is the enzyme quantity producing a reducing sugar in an amount equivalent to 1 mg of maltotetraose per hour) prepared from Pseudomonas stutzeri IFO 3773, and maltotetraose formation was effected by gentle shaking at 40° C. for 2 hours.

Further, each reaction mixture was applied to Dowex 50W-X2 and the effluent (unadsorbed fraction) was collected. A TLC of such maltotetraose fraction as obtained after 20 minutes of amylase treatment is shown in FIG. 12 for each case.

Figure 12:
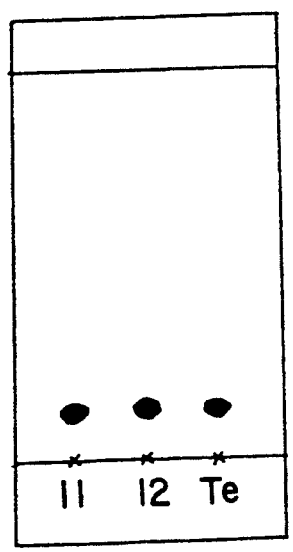
FIG. 12 shows the TLCs of the maltotetraose fractions sampled in Example 10. In the figure, 11 indicates the maltotetraose fraction from the N-propylmoranoline-based chain transfer product, 12 the maltotetraose fraction from the N-benzylmoranoline-based product, and Te maltotetraose.

From FIG. 12, it is evident that maltotetraose alone was produced.

Analysis by the 3,5-dinitrosalicylic acid method using a reference standard of maltotetraose confirmed the formation of 2.0 mg and 1.6 mg, respectively, of maltotetraose.

EXAMPLE 11

An N-propylmoranoline-based or N-benzylmoranoline-based saccharide chain transfer product (to 12.5 mg) obtained in the same manner as in Example 1 was admixed with 250 μl of a solution of a maltopentaose-producing amylase (10.13 units/1.85 mg protein; one unit is the quantity of enzyme producing a reducing sugar in an amount equivalent to 1 mg of maltopentaose) prepared from Pseudomonas sp. KO-8940 (FERM P-7456), and maltopentaose production was effected with gentle shaking at 40° C. for 2 hours.

Further, each reaction mixture was applied to Dowex 50W-X2 and the effluent (unadsorbed fraction) was collected. A TLC of the maltopentaose fraction from said N-benzylmoranoline-based transfer product as obtained after 90 minutes of amylase treatment is shown in FIG. 13.

Figure 13:
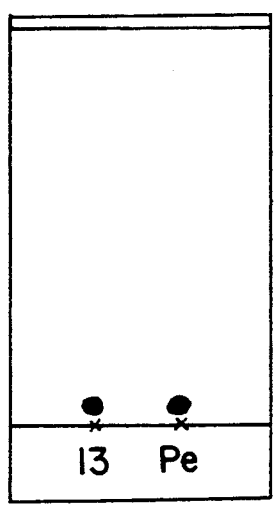
FIG. 13 shows the TLC of the maltopentaose fraction sampled in Example 11. In the figure, 13 indicates the maltopentaose fraction from the N-benzylmoranoline-based chain transfer product and Pe maltopentaose.

From FIG. 13, it is evident that maltopentaose alone was produced.

Analysis by the 3,5-dinitrosalicylic acid method using a reference standard of maltopentaose confirmed the formation of 0.6 mg and 0.8 mg, respectively, of maltopentaose.

We claim:

1. A process for producing a pure oligosaccharide having a chain length of from 2 to 6 glucose units, said process comprising the steps of:
   a) forming oligosaccharides of arbitrary chain length of glucose units at least as long as said pure oligosaccharide, with a carrier material attached to an end thereof, from a reaction mixture of said carrier material, saccharide glucose chain donors and glycosyltransferase;
   b) cleaving oligosaccharide units of the same chain length as said pure oligosaccharide from said oligosaccharides of arbitrary chain length, with attached carrier material, by means of an exo-cleaving carbohydrolase, suitable for cleaving said oligosaccharide units; and
   c) separating the oligosaccharide units from residual material having said carrier material, with said carrier material providing means for substantially completely effecting said separation.

2. The process for producing a pure oligosaccharide as claimed in claim 1, wherein said carrier material is a compound of the general formula (I)

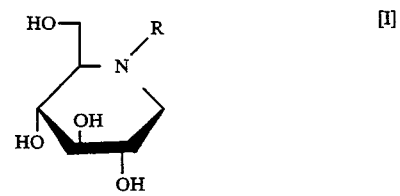

(wherein R is hydrogen, lower alkyl, hydroxyalkyl, phenylalkyl, phenylalkenyl, phenylalkynyl, phenoxyalkyl, phenoxyalkenyl, or phenoxyalkynyl; including the substituted phenyl compounds described hereinbefore), nojirimycin, aminocyclitols, aminocyclitol derivatives or glucuronic acid derivatives, or glucosylated or oliglucosylated products thereof.

3. A process according to claim 2, wherein said substantially separable substance is a carrier.

4. A process according to claim 3, wherein said carrier is chitosan beads.

5. A process according to claim 2, wherein said substantially separable substance is a compound of the general formula (I)

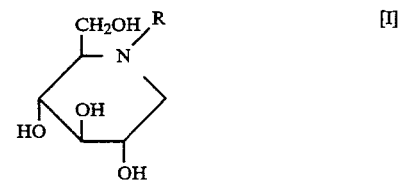

wherein R is hydrogen, lower alkyl, hydroxyalkyl, phenylalkyl, phenylakenyl, phenylalkynyl, phenoxyalkyl, phenoxyalkenyl or phenoxyalkynyl, including the case where the phenyl moiety is substituted; or a glucosylated or oligoglucosylated modification product thereof.

6. A process according to claim 5, wherein R is lower alkyl.

7. A process according to claim 5, wherein R is phenylalkyl.

* * * * *